United States Patent
Hakim

(10) Patent No.: US 7,050,619 B2
(45) Date of Patent: May 23, 2006

(54) METHOD AND DEVICE FOR AUTOMATIC DETECTION OF A GRADUATED COMPRESSION PADDLE

(75) Inventor: Souheil Hakim, Beruit (LB)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 346 days.

(21) Appl. No.: 10/034,502

(22) Filed: Dec. 27, 2001

(65) Prior Publication Data

US 2004/0001630 A1    Jan. 1, 2004

(30) Foreign Application Priority Data

Jan. 11, 2001  (FR) .................................. 01 00339

(51) Int. Cl.
*G06K 9/00*    (2006.01)

(52) U.S. Cl. .................... 382/133; 382/132; 382/128

(58) Field of Classification Search ............... 382/278, 382/132, 280, 133
See application file for complete search history.

(56) References Cited

U.S. PATENT DOCUMENTS

| | | | |
|---|---|---|---|
| 4,875,478 A * | 10/1989 | Chen | 600/429 |
| 4,952,772 A * | 8/1990 | Zana | 219/124.34 |
| 4,993,056 A * | 2/1991 | Lary | 378/164 |
| 5,156,150 A * | 10/1992 | Lary | 600/310 |
| 5,163,099 A * | 11/1992 | Osaki et al. | 382/191 |
| 5,526,394 A * | 6/1996 | Siczek et al. | 378/37 |
| 5,579,360 A * | 11/1996 | Abdel-Mottaleb | 378/37 |
| 5,598,269 A * | 1/1997 | Kitaevich et al. | 356/399 |
| 6,647,089 B1 * | 11/2003 | Virta et al. | 378/37 |

FOREIGN PATENT DOCUMENTS

| | | |
|---|---|---|
| EP | 0465367 | 1/1995 |
| EP | 0402244 | 10/1995 |
| EP | 0723762 | 7/1996 |
| FR | 2786389 | 6/2000 |
| WO | 9746971 | 12/1997 |

OTHER PUBLICATIONS

Press, William H., Teukolsky, Saul A., Vetterling, William T., Flannery, Brian P., Numerical Recipes in Fortran 77, 1992, Cambridge University Press, 2nd Edition, ISBN 0-521-43064-X.*

Baxes, Gregory A., Digital Image Processing, 1994, John Wiley & Sons, Inc., ISBN 0-471-00949-0.*

* cited by examiner

Primary Examiner—Bhavesh M. Mehta
Assistant Examiner—Sath V. Perungavoor
(74) Attorney, Agent, or Firm—Cantor Colburn LLP

(57) ABSTRACT

An acquisition is made of a base digital image containing the paddle, and the base image is subdivided into rows of N elementary pixels respectively assigned luminous intensity values, the rows of elementary pixels all being parallel to a general direction of graduation of the paddle. N autocorrelations of the vector of luminous intensity values associated with the row of elementary pixels are made for each row, with respectively the vector and the N−1 vectors successively shifted by 1 elementary pixel, so as to obtain for each row a vector of N autocorrelation values. A Fourier transform treatment is carried out on each autocorrelation vector, in order to obtain an energy frequency spectrum. The energy value at the frequency of the graduated marks is compared for each spectrum with a predetermined threshold value and the presence of the paddle is deduced therefrom.

9 Claims, 6 Drawing Sheets

METHOD AND DEVICE FOR AUTOMATIC DETECTION OF A GRADUATED COMPRESSION PADDLE

CROSS REFERENCE TO RELATED APPLICATIONS

This application claims the benefit of a priority under 35 USC 119 to French Patent Application No. 01 00339 filed Jan. 11, 2001, the entire contents of which are incorporated by reference.

BACKGROUND OF THE INVENTION

The invention concerns digital radiology, notably digital mammography and, in particular, the automatic detection of a graduated compression paddle of a mammography apparatus.

In mammography, a compression paddle is a support making it possible to receive under compression the breast of the person to be observed. A compression paddle includes a graduation appearing on two perpendicular sides of a rectangular opening in the compression surface.

As is standard, in radiology, the exposure parameters such as the focal path chosen (in the case of a device with double focal path), the filter used, the voltage applied to the tube (kV), the presence or absence of grid, the contact magnification and the product of the anode current by the exposure time (m A.s), constituting what is called the configuration, are initially determined from a user's choice for the parameters of grid presence or absence, magnification or contact and a table of automatic optimization of parameters (AOP), as function of the user's choice, for the parameters kV, focal path, filter and m A.s. The organ part examined then undergoes a pre-exposure with a low m A.s value in order to determine the characteristics of the organ part examined, particularly the equivalent radiological thickness, and the exposure parameters are then adjusted from those characteristics. The mode of automatic acquisition known as AOP is disclosed in EP-0,402,244, EP-0,465,360 and FR-2,786,389.

In an AOP automatic mode, optimization of the parameters of the tube is a function of the most glandular area of the breast. The most glandular area of the breast is expressed as being the lowest brightness level observed on a cell in the order of 1 cm2 in the pre-exposure image. The plumb marks of graduation of the compression paddle, combined with the thickness of the region of the breast under the marks, contribute to weakening the signal in the image. Consequently, the effects of attenuation of the marks can cause a poor detection of the most glandular area of the breast. In fact, the combination of the marks and of the area of the breast situated under those marks produces a greater attenuation than that of the most glandular area of the breast. The parameters of the tube are, consequently, optimized on that combination of "marks and breast area," situated under the marks, rather than on the most glandular area of the breast.

Further, the use of parameters of the tube not optimized can lead to irregular X-ray doses, which may affect image quality.

BRIEF DESCRIPTION OF THE INVENTION

An embodiment of the invention proposes an automatic detection of a graduated compression paddle. An embodiment of the invention is a method of automatic detection of a graduated compression paddle of a mammography apparatus, in which an acquisition is made of a base digital image containing the paddle, and the base image is subdivided into rows of N elementary pixels respectively assigned luminous intensity values, the rows of elementary pixels all being parallel to a general direction of graduation of the paddle. N autocorrelations of the vector of luminous intensity values associated with the row of elementary pixels are made for each row, with respectively the vector and the N−1 vectors successively shifted by 1 elementary pixel, so as to obtain for each row a vector of N autocorrelation values. A Fourier transform treatment is carried out on each autocorrelation vector, in order to obtain an energy frequency spectrum. The energy value at the frequency of the graduated marks is compared for each spectrum with a predetermined threshold value and the detection of the paddle is deduced therefrom.

An embodiment of the invention is also directed to a device for automatic detection of a graduated compression paddle of a mammography apparatus, comprising means for acquisition of a digital base image containing the paddle and means for subdivision of the base image into rows of N elementary pixels respectively assigned luminous intensity values, the rows of elementary pixels all being parallel to a general direction of graduation of the paddle.

The device may also comprise means for autocorrelation capable of carrying out for each row N autocorrelations of the vector of luminous intensity values associated with the row of elementary pixels, with respectively the vector and the N−1 vectors successively shifted by 1 elementary pixel, so as to obtain for each row a vector of N autocorrelation values.

The device may further comprise means for treatment capable of carrying out a Fourier transform treatment on each autocorrelation vector, so as to obtain an energy frequency spectrum, and means for comparison capable of comparing the energy value at the frequency of the graduated marks with a predetermined threshold value for each spectrum. Means for detection are then capable of deducing the presence of the paddle from the result of the comparison.

An embodiment of the invention is also directed to a device for automatic detection of a graduated compression paddle of a mammography apparatus, capable of applying the method, as disclosed.

An embodiment of the invention is also directed to a computer program product, recorded on a support usable in a processor, comprising means for program code employing the disclosed method when the product is executed within the processor.

BRIEF DESCRIPTION OF THE DRAWINGS

Other advantages and characteristics of the invention will appear on examination of the detailed description of non-limitative methods of use and embodiments and of the attached drawings, in which.

DETAILED DESCRIPTION OF THE INVENTION

According to an embodiment of the invention, the base image is subdivided into rows of N cells of n×n base pixels and each cell is transformed into an elementary pixel, the luminous intensity value of the elementary pixel being equal to the mean of the luminous intensity values respectively associated with the base pixels of the cell.

Acquisition of the image is carried out in an automatic mode, in which the adjustment of the exposure parameters is determined from a table of automatic optimization of parameters (AOP).

According to an embodiment of the invention, the means for subdivision are capable of subdividing the base image into rows of N cells of n×n base pixels. The means for subdivision then comprises means for transformation capable of transforming each cell into an elementary pixel, the luminous intensity value of the elementary pixel being equal to the mean of the luminous intensity values respectively associated with the base pixels of the cell.

Figure 1:
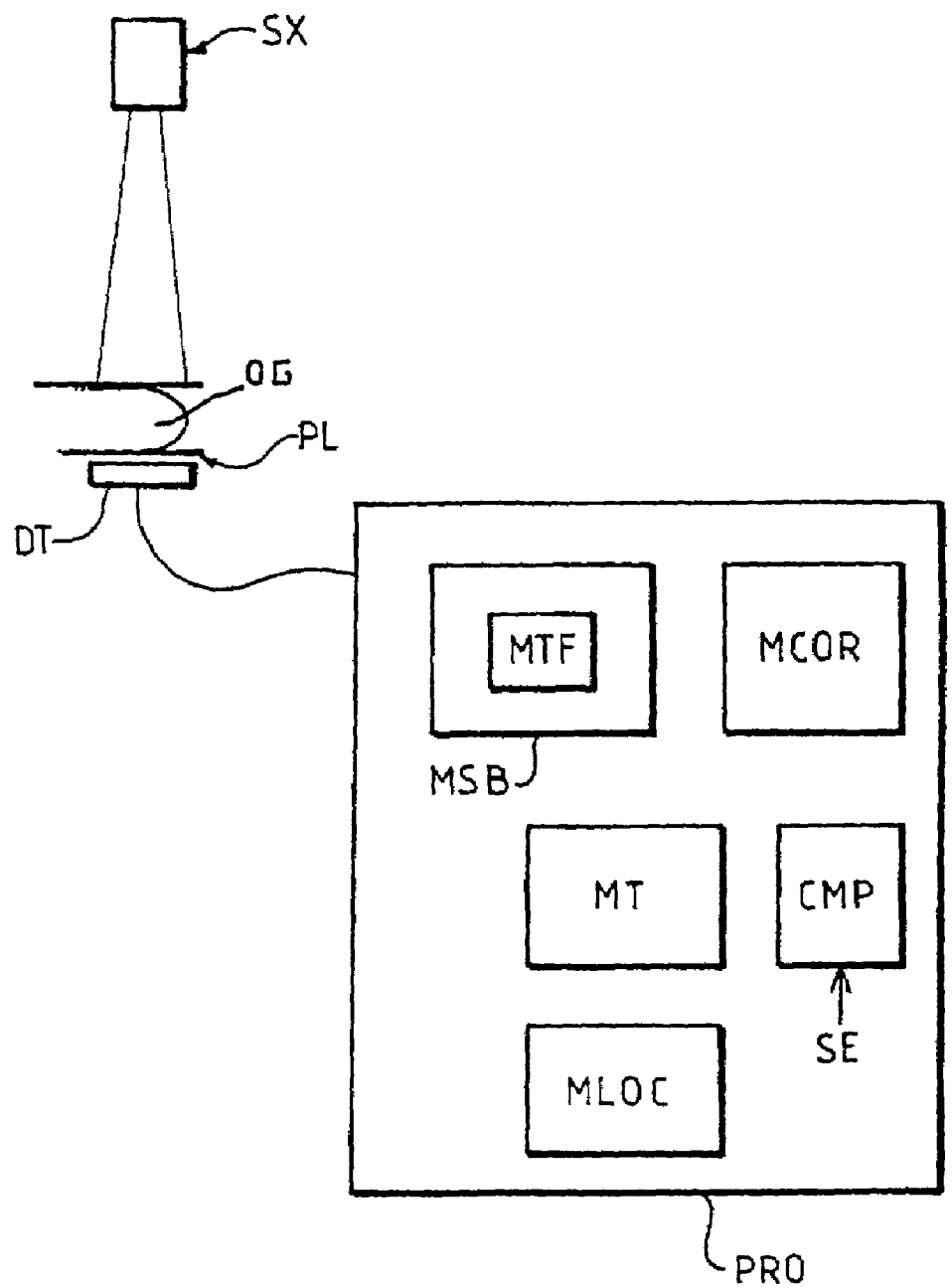
FIG. 1 schematically illustrates an embodiment of a device according to an embodiment of the invention.
Figure 3:
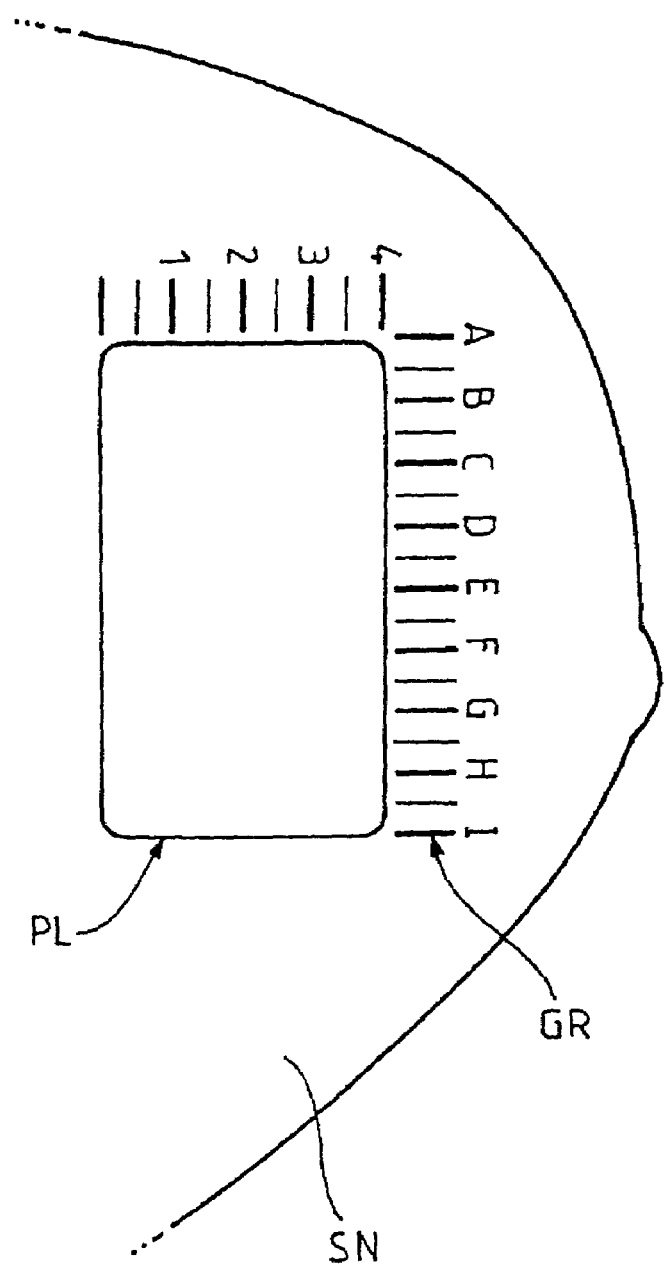
FIGS. 3 to 6 also schematically illustrate some stages of a mode of use of the method according to an embodiment of the invention.
Figure 4:
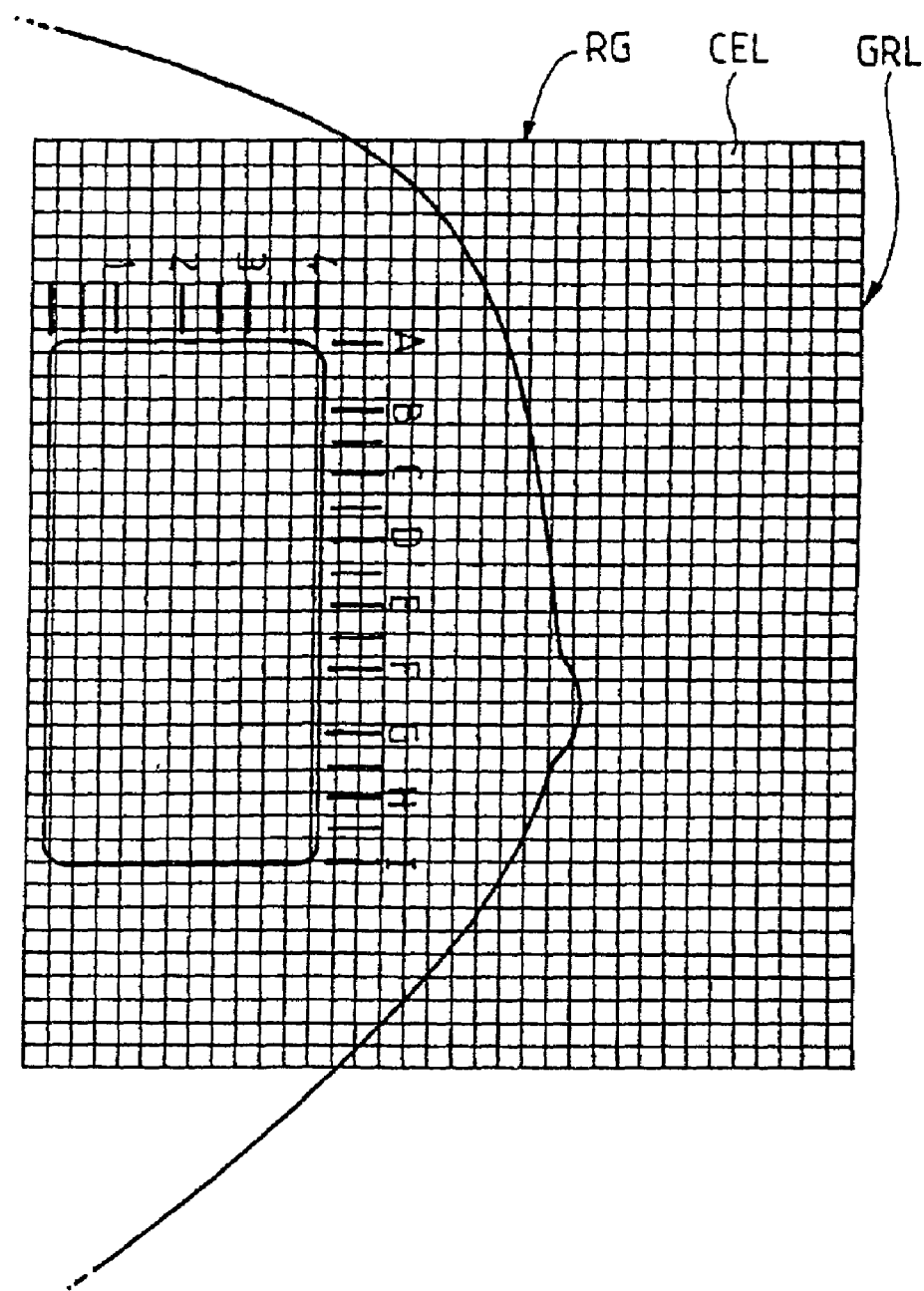

In FIG. 1, reference SX designates an X-ray tube emitting an X-ray beam in the direction of an organ OG to be examined, in this case a breast. The breast is compressed in a compression paddle PL. Such compression paddle PL is illustrated in more detail in FIG. 3. In FIG. 3 the compression paddle contains an opening with a graduation GR formed by equidistant plumb marks on two perpendicular sides.

The device according to an embodiment of the invention comprises means for acquisition DT of a digital image, such as a sensor CCD, placed under the paddle PL and connected to a processor PRO of a computer which incorporates all the other means according to an embodiment of the invention. Those other means, which comprise, for example, of software, are means for subdivision MSB containing means for transformation MTF, means of autocorrelation MCOR, means for treatment MT, means for comparison CMP and means of detection MLOC.

Figure 2:
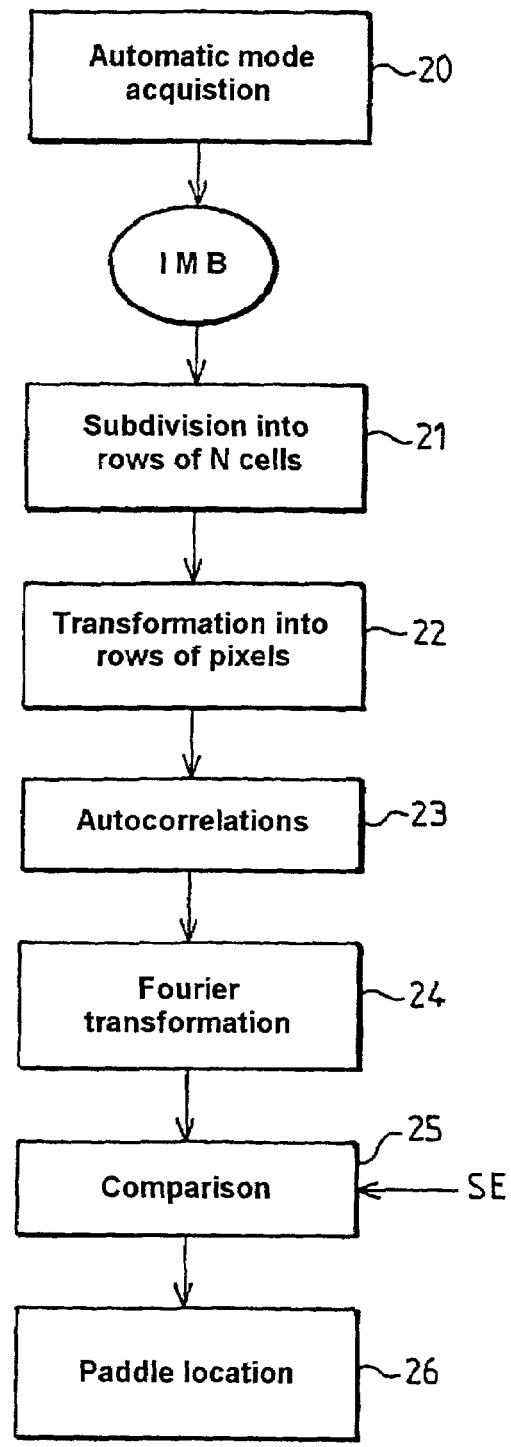
FIG. 2 schematically illustrates the principal stages of a mode of use of the method according to an embodiment of the invention.

FIG. 2 and the following figures describe a mode of use of the method.

In stage 20, an acquisition is undertaken in automatic mode (AOP). As indicated above, such acquisition in automatic mode is known.

A base image IMB is then obtained, which the means for subdivision MSB subdivide (stage 21) into rows RG of N cells CEL. The base image IMB acquired in automatic mode is a search region called "AOP region," which is subdivided into rows of N cells. Each cell contains n×n pixels called "base pixels."

The means for transformation MTF transforms (stage 22) each cell CEL into an elementary pixel, the luminous intensity value of which is equal to the mean of the luminous intensity values respectively associated with the base pixels of the cell. After the transformation, rows of N elementary pixels are then obtained.

The means for autocorrelation MCOR then carry out for each row (stage 23) N autocorrelation of the vector of luminous intensity values associated with the row of elementary pixels, with respectively that vector and the N−1 vectors successively shifted by 1 elementary pixel, so as to obtain for each row a vector of N autocorrelation values. More precisely, each value of the autocorrelation vector of a row is defined by the following formula:

$$R(L_i) = \frac{\sum_{k=0}^{N-L_i-1}(x_k + L_i - \bar{x})(x_k - \bar{x})}{\sum_{k=0}^{N-1}(x_k - \bar{x})^2}$$

In this formula, $R(L_i)$ designates each autocorrelation value of the vector, ($L_i$ varying from 0 to N−1), $x_k$ designates the luminous intensity value of the elementary pixel of row k and x designates the mean luminous intensity of all the elementary pixels.

The means for treatment MT carry out a Fourier transform treatment on each autocorrelation value, so as to obtain an energy frequency spectrum. The energy value at the spacing frequency FO of the graduated marks is then compared for each spectrum with a predetermined threshold value SE.

Figure 6:
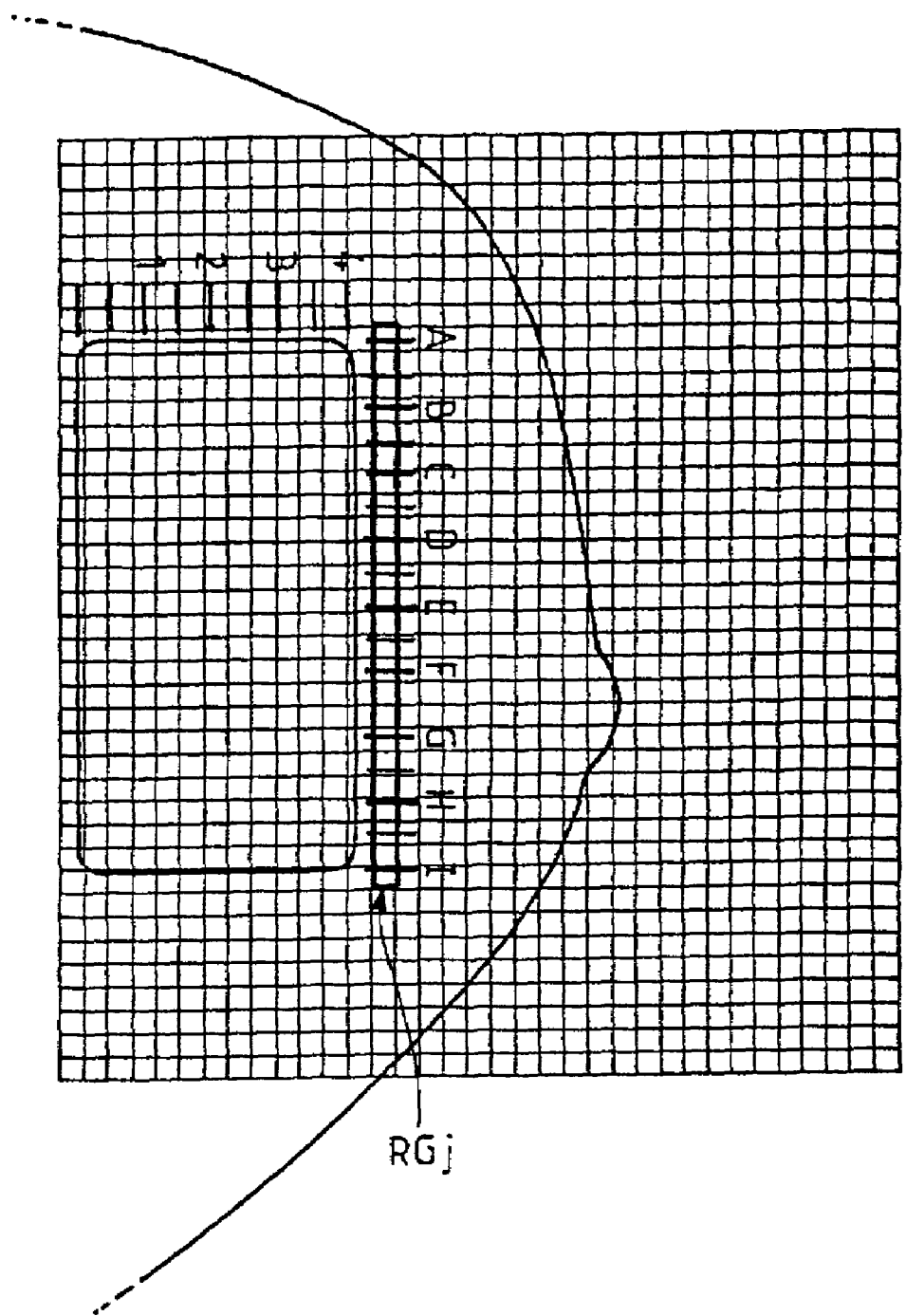

The energy spectrum associated with row RGj (FIG. 6), which is a row over-lapping the plumb marks presents a strong concentration at the nominal frequency FO of spacing of the marks.

Figure 5:
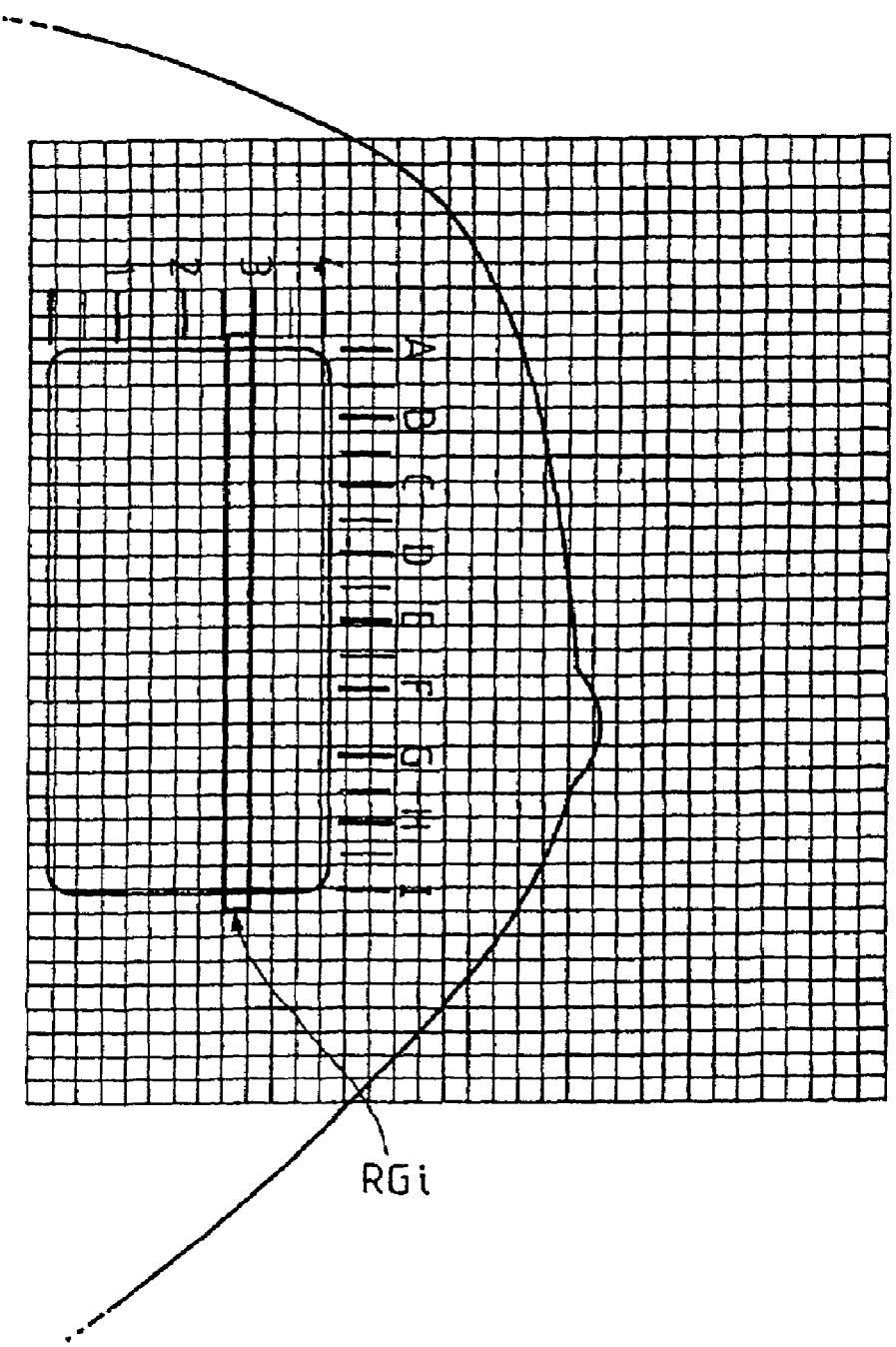

Alternatively, the energy spectrum associated with row RGi (FIG. 5), which does not correspond to the plumb graduation, will not present that energy peak at frequency FO.

The comparison indicated above permits the detection of the compression paddle very precisely and, consequently, to distinguish the densest area of the breast SN from the area of the paddle unambiguously.

Various modifications in structure and/or steps and/or function may be made by one skilled in the art without departing from the scope and extent of the invention as recited in the claims.

What is claimed is:

1. A method of automatic detection of a graduated compression paddle used for breast analysis in digital mammography, the method comprising:
   acquiring a base digital image containing the paddle and at least a portion of the breast, the base image being subdivided into rows of N elementary pixels respectively assigned luminous intensity values, the rows of elementary pixels all being parallel to a general direction of graduation of the paddle;
   determining N autocorrelations of the vector of luminous intensity values associated with the row of elementary pixels are made for each row, with respectively the vector and the N−1 vectors successively shifted by 1 elementary pixel, so as to obtain for each row a vector of N autocorrelation values;
   carrying out a Fourier transform treatment on each autocorrelation vector, in order to obtain an energy frequency spectrum;
   comparing the energy value at the frequency of the graduated marks for each spectrum with a predetermined threshold value;
   detecting the paddle; and
   unambiguously distinguishing a densest area of the breast from an area of the paddle containing the graduated marks, thereby enabling automatic exposure adjustment based on a most glandular area of the breast;
   wherein the acquisition of the image is carried out in an automatic mode, in which an adjustment of the exposure parameters is determined from table of automatic optimization of parameters (AOP).

2. The method according to claim 1 wherein the base image is subdivided into rows of N cells of n×n base pixels and each cell is transformed into an elementary pixel, the luminous intensity value of the elementary pixel being equal to the mean of the luminous Intensity values respectively associated wit the base pixels of the cell.

3. A device for automatic detection of a graduated compression paddle used for breast analysis in digital mammography, the device comprising:
   means for acquisition of a digital base image containing the paddle end at least a portion of the breast;
   means for subdivision of the base image into rows of N elementary pixels respectively assigned luminous intensity values, the rows of elementary pixels all being parallel to a general direction of graduation of the paddle;
   means capable of carrying out for each row N autocorrelations of the vector of luminous intensity values associated with the row of elementary pixels, with respectively the vector and the N−1 vectors successively shifted by 1 elementary pixel, so as to obtain for each row a vector of N autocorrelation values;
   means for treatment capable of carrying out a Fourier transform treatment on each autocorrelation vector, so as to obtain an energy frequency spectrum;
   means for comparison capable of comparing the energy value at the frequency of the graduated marks with a predetermined threshold value for each spectrum; and
   means for detection capable of deducing the presence of the paddle from the result of the comparison and unambiguously distinguishing a densest area of the breast from an area of the paddle containing the graduated marks, thereby enabling automatic exposure adjustment based on a most glandular area of the breast.

4. The device according to claim 3 wherein the means for subdivision are capable of subdividing the base image into rows of N cells of n×n base pixels, and contain means for transformation capable of transforming each cell into an elementary pixel, the luminous intensity value of the elementary pixel being equal to the mean of the luminous intensity values respectively associated with the base pixels of the cell.

5. A device far automatic detection of a graduated compression paddle capable of applying the method according to claim 1.

6. Computer program product, recorded on a computer readable medium usable by a processor, containing program code means employing the method according to claim 1 when the product is executed by the processor.

7. The method according to claim 1, wherein the comparing the energy value at the frequency of the graduated marks comprises:
   comparing the energy yaks at the spacing frequency of the graduated marks.

8. The device according to claim 3, wherein the means for comparison capable of comparing the energy value at the frequency of the graduated marks with a predetermined threshold value for each spectrum comprises:
   means for comparison capable of comparing the energy value at the spacing frequency of the graduated marks with a predetermined threshold value for each spectrum.

9. A method of automatic detection of a graduated compression paddle used for organ analysis in digital mammography, the method comprising:
   acquiring a base digital image containing the paddle and at least a portion of the organ, the base image being subdivided into rows of N elementary pixels respectively assigned luminous intensity values, the rows of elementary pixels all being parallel to a general direction of graduation of the paddle;
   determining N autocorrelations of the vector of luminous intensity values associated with the row of elementary pixels are made for each row, with respectively the vector and the N−1 vectors successively shifted by 1 elementary pixel, so as to obtain for each raw a vector of N autocorrelation values;
   carrying out a Fourier transform treatment on each autocorrelation vector, in order to obtain an energy frequency spectrum;
   comparing the energy value at the spacing frequency of the graduated marks for each spectrum with a redetermined threshold value;
   detecting the paddle; and
   unambiguously distinguishing a densest area of the organ from an area of the paddle containing the graduated marks, thereby enabling automatic exposure adjustment based on a most glandular area of the organ.

* * * * *